(12) United States Patent
Cole

(10) Patent No.: US 7,649,189 B2
(45) Date of Patent: Jan. 19, 2010

(54) CRDS MIRROR FOR NORMAL INCIDENCE FIBER OPTIC COUPLING

(75) Inventor: Barrett E. Cole, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/137,007

(22) Filed: Jun. 11, 2008

(65) Prior Publication Data

US 2008/0239299 A1    Oct. 2, 2008

Related U.S. Application Data

(63) Continuation-in-part of application No. 11/770,648, filed on Jun. 28, 2007, which is a continuation-in-part of application No. 11/633,872, filed on Dec. 4, 2006.

(51) Int. Cl.
G01N 15/06 (2006.01)
G01N 21/49 (2006.01)
G01N 21/85 (2006.01)

(52) U.S. Cl. .................. 250/573; 250/576; 356/437; 356/440

(58) Field of Classification Search .................. 250/573, 250/576; 356/437, 440
See application file for complete search history.

(56) References Cited

U.S. PATENT DOCUMENTS

| | | | |
|---|---|---|---|
| 4,233,568 A | 11/1980 | Hamerdinger et al. | |
| 4,612,647 A | 9/1986 | Norvell | |
| 4,614,961 A | 9/1986 | Khan et al. | |
| 4,672,624 A * | 6/1987 | Ford | 372/87 |
| 4,870,224 A | 9/1989 | Smith et al. | |
| 4,973,131 A | 11/1990 | Carnes | |
| 5,022,745 A | 6/1991 | Zayhowski et al. | |
| 5,040,895 A | 8/1991 | Laurent et al. | |
| 5,135,304 A | 8/1992 | Miles et al. | |
| 5,146,465 A | 9/1992 | Khan et al. | |
| 5,278,435 A | 1/1994 | Van Hove et al. | |
| 5,311,280 A | 5/1994 | Koper et al. | |

(Continued)

FOREIGN PATENT DOCUMENTS

| | | |
|---|---|---|
| DE | 3311808 | 10/1984 |
| DE | 19635421 | 12/1997 |
| EP | 0177918 | 3/1991 |
| EP | 0667548 | 1/1995 |
| EP | 1069658 | 1/2001 |

(Continued)

OTHER PUBLICATIONS

Bernstein et al., "Development of a Miniature Silicon PhotoAcoustic Gas Sensor", Presented at Opto 96, Leipzig, Germany, 6 pages, Sep. 26-29, 1999.

(Continued)

*Primary Examiner*—Seung C Sohn
(74) *Attorney, Agent, or Firm*—Kris T. Fredrick (57) ABSTRACT

A cavity ring-down sensor having an optical path of mirrors and an interface proximate to a mirror with a normal incidence optical fiber coupling. The interface may be a block of transmissive materials having different indices of refraction for receiving a light beam of normal incidence from an optical fiber and directing the beam into the optical path. The sensor may be used applications where the optical fiber needs to be straight into the sensor without unusual bending because of space limitations. One application of this sensor may be for ground water testing via a narrow well casing.

18 Claims, 8 Drawing Sheets

U.S. PATENT DOCUMENTS

| | | | |
|---|---|---|---|
| 5,408,319 A | 4/1995 | Halbout et al. | |
| 5,418,868 A | 5/1995 | Cohen et al. | |
| 5,450,053 A | 9/1995 | Wood | |
| 5,468,910 A | 11/1995 | Knapp et al. | |
| 5,512,750 A | 4/1996 | Yanka et al. | |
| 5,528,040 A | 6/1996 | Lemann | |
| 5,550,373 A | 8/1996 | Cole et al. | |
| 5,629,951 A | 5/1997 | Chang-Hasnain et al. | |
| 5,677,538 A | 10/1997 | Moustakas et al. | |
| 5,679,965 A | 10/1997 | Schetzina | |
| 5,723,706 A | 3/1998 | Brasier et al. | |
| 5,739,554 A | 4/1998 | Edmond et al. | |
| 5,815,277 A | 9/1998 | Zare et al. | |
| 5,832,017 A | 11/1998 | Ramdani et al. | |
| 5,834,331 A | 11/1998 | Razeghi | |
| 5,835,231 A * | 11/1998 | Pipino | 356/440 |
| 5,847,397 A | 12/1998 | Moustakas | |
| 5,869,896 A | 2/1999 | Baker et al. | |
| 5,900,650 A | 5/1999 | Nitta | |
| 5,909,280 A | 6/1999 | Zavracky | |
| 5,912,740 A | 6/1999 | Zare et al. | |
| 5,915,051 A | 6/1999 | Damask et al. | |
| 5,933,565 A | 8/1999 | Diebold | |
| 5,960,025 A | 9/1999 | Thorland et al. | |
| 6,040,895 A | 3/2000 | Haas | |
| 6,080,988 A | 6/2000 | Ishizuya et al. | |
| 6,084,682 A | 7/2000 | Zare et al. | |
| 6,091,504 A | 7/2000 | Walker et al. | |
| 6,115,122 A | 9/2000 | Bao et al. | |
| 6,122,416 A | 9/2000 | Ooba et al. | |
| 6,147,756 A | 11/2000 | Zavracky et al. | |
| 6,208,798 B1 | 3/2001 | Morozov et al. | |
| 6,233,052 B1 * | 5/2001 | Zare et al. | 356/437 |
| 6,287,940 B1 | 9/2001 | Cole et al. | |
| 6,295,130 B1 | 9/2001 | Sun et al. | |
| 6,296,779 B1 | 10/2001 | Clark et al. | |
| 6,310,904 B1 | 10/2001 | Thorland et al. | |
| 6,324,192 B1 | 11/2001 | Tayebati | |
| 6,335,669 B1 | 1/2002 | Miyazaki et al. | |
| 6,380,531 B1 | 4/2002 | Sugihwo et al. | |
| 6,384,953 B1 | 5/2002 | Russell et al. | |
| 6,404,648 B1 | 6/2002 | Slupe et al. | |
| 6,406,578 B1 | 6/2002 | Schober et al. | |
| 6,421,127 B1 | 7/2002 | McAndrew et al. | |
| 6,424,419 B1 * | 7/2002 | Tazartes et al. | 356/473 |
| 6,438,149 B1 | 8/2002 | Tayebati et al. | |
| 6,452,680 B1 * | 9/2002 | Paldus et al. | 356/436 |
| 6,483,130 B1 | 11/2002 | Yang et al. | |
| 6,492,726 B1 | 12/2002 | Quek et al. | |
| 6,507,107 B2 | 1/2003 | Vaiyapuri | |
| 6,545,739 B1 | 4/2003 | Matsumoto et al. | |
| 6,583,917 B2 | 6/2003 | Melloni et al. | |
| 6,584,126 B2 | 6/2003 | Wang et al. | |
| 6,590,710 B2 | 7/2003 | Hara et al. | |
| 6,594,059 B2 | 7/2003 | Flanders | |
| 6,597,713 B2 | 7/2003 | Ouchi | |
| 6,608,711 B2 | 8/2003 | Flanders et al. | |
| 6,627,983 B2 | 9/2003 | Tu et al. | |
| 6,658,034 B2 | 12/2003 | Garnache et al. | |
| 6,670,599 B2 | 12/2003 | Wagner et al. | |
| 6,728,286 B2 | 4/2004 | Thorland et al. | |
| 6,816,636 B2 | 11/2004 | Cole et al. | |
| 6,836,501 B2 | 12/2004 | Cox et al. | |
| 6,879,014 B2 | 4/2005 | Wagner et al. | |
| 6,985,281 B2 | 1/2006 | Wagner et al. | |
| 7,002,697 B2 | 2/2006 | Domash et al. | |
| 7,012,696 B2 | 3/2006 | Orr et al. | |
| 7,015,457 B2 | 3/2006 | Cole et al. | |
| 7,046,362 B2 | 5/2006 | Lehmann et al. | |
| 7,049,004 B2 | 5/2006 | Domash et al. | |
| 7,089,781 B2 | 8/2006 | Petrovic et al. | |
| 7,106,763 B2 | 9/2006 | Tan et al. | |
| 7,113,256 B2 | 9/2006 | Butler et al. | |
| 7,145,165 B2 | 12/2006 | Cox et al. | |
| 7,147,165 B2 | 12/2006 | Mongin et al. | |
| 7,147,695 B2 | 12/2006 | Mitra | |
| 7,221,827 B2 | 5/2007 | Domash et al. | |
| 7,263,871 B2 | 9/2007 | Selker et al. | |
| 7,304,799 B2 | 12/2007 | Ma et al. | |
| 7,369,242 B2 | 5/2008 | Cole et al. | |
| 2002/0191268 A1 | 12/2002 | Seeser et al. | |
| 2003/0107739 A1 * | 6/2003 | Lehmann et al. | 356/437 |
| 2004/0234198 A1 | 11/2004 | Wagner et al. | |
| 2004/0255853 A1 | 12/2004 | Ma et al. | |
| 2005/0030628 A1 | 2/2005 | Wagner et al. | |
| 2005/0082480 A1 | 4/2005 | Wagner et al. | |
| 2005/0105184 A1 | 5/2005 | Ma et al. | |
| 2005/0254056 A1 | 11/2005 | Kachanov et al. | |
| 2005/0286054 A1 * | 12/2005 | Chen et al. | 356/437 |
| 2007/0133001 A1 | 6/2007 | Cox et al. | |
| 2008/0151248 A1 | 6/2008 | Cole et al. | |

FOREIGN PATENT DOCUMENTS

| | | |
|---|---|---|
| EP | 1061618 | 11/2007 |
| JP | 03252172 | 11/1991 |
| JP | 05095130 | 4/1993 |
| JP | 7288334 | 10/1995 |
| WO | 9326049 | 12/1993 |
| WO | 9942875 | 8/1999 |

OTHER PUBLICATIONS

Brown, et al., "Visible-Blind UV Digital Camera Based on a 32*32 Array of GAN/AIGAN P-I-N Photodiodes", MRS Internet Journal of Nitride Semiconductor Research, vol. 4S1, pp. 1-10, Sep. 1999.

Campargue et al., "Measurement of SiH2 Density in a Discharge by Intracavity Laser Absorption Spectroscopy and CW Cavity Ring-Down Spectroscopy," Journal of Physics D. Applied Physics, vol. 31, No. 10 pp. 1168-1175, May 21, 1998.

Chitica et al., "Monolithic InP-based Tunable Filter with 10-nm Bandwidth for Optical Data Interconnects in the 1550-nm Band," IEEE Photonics Technology Letters, vol. 11, No. 5, pp. 584-586, May 1999.

Chou et al., "Diode-Laser Measurements of He-, Ar-, and N2-Broadened HF Lineshapes in the First Overtone Band," Journal of Molecular Spectroscopy 196, pp. 70-76, 1999.

Chung et al., "Design and Fabrication of 10×10 Micro-Spatial Light Modulator Array for Phase and Amplitude Modulation," Sensors and Actuators, vol. 78, No. 1, pp. 63-70, Jan. 1999.

Cole et al., "Microscopic Spectroscopy of Optical MEMS Devices," Topic 2 (Materials and Technology), Honeywell Laboratories, 2 pages, on or Around Dec. 11, 2000.

Edwards, "Multiple-Traverse Absorption Cell Design," Journal of the Optical Society of America, vol. 51, No. 1, pp. 98-102, Jan. 1961.

Ferber et al., "A Miniature Silicon Photoacoustic Detector for Gas Monitoring Applications", presented at the MTEX International Conference on Sensors and Transducers, Birmingham, UK, 7 pages, Feb. 14, 2001.

Jerman et al., "A Miniature Fabry-Perot Interferometer with a Corrugated Silicon Diaphragm Support," Sensors and Actuators, vol. A29, No. 2, pp. 151-158, Nov. 1991.

Kurochkin et al., "Complex-Cavity Two-Mode CO2 Laser for Saturated Intracavity Absorption Spectroscopy," Optical Spectroscopy, vol. 68, No. 6, pp. 793-797, 1990.

Kurochkin et al., "Three-Mirror Cavity CO2 Laser Intracavity Saturated-Absorption Spectroscopy," Optical Spectroscopy, vol. 65, No. 2, pp. 265-267, 1988.

O'Keefe et al., "Cavity Ring-Down Optical Spectrometer for Absorption Measurements Using Pulsed Laser Sources," Review of Scientific Instruments, 59, 11 pages, 1988.

Paul et al., "Cavity Ringdown Measures Trace Concentrations," Laser Focus World, pp. 71-80, Mar. 1997.

Richman et al., "Continuously Tunable, Single-Longitudinal-Mode, Pulsed Mid-Infrared Optical Parametric Oscillator Based on Periodically Poled Lithium Niobate," Optical Society of America, vol. 17, No. 7, pp. 1233-1239.

Sadeghi et al., "Cavity Ring Down Spectroscopy Applied to Plasma Diagnostics," Proc. Int. Symp. Laser-aided Plasma Diagnostics Lake Tahoe, CA, , 8 pages, Sep. 1999.

Scherer et al., "Infrared Cavity Ringdown Laser Absorption Spectroscopy (IR-CRLAS) in Low Pressure Flames," Applied Physics B., vol. 64, pp. 699-705, 1997.

Schweber, "An Old Communications Problem Reoccures in Optical-Communication-System Design—How it Works: Making the Laser Diode Tunable", EDN, 3 pages, Sep. 28, 2000.

Shimizu et al., "Stark Spectroscopy by 10µ Lasers Using a Multipath Cell," Journal of Applied Physics, vol. 46, No. 1, pp. 258-259, Jan. 1975.

Smirnov et al., "Dye Lasers Using a Three-Mirror Cavity with Lamp Excitation," 4 pages, 1981.

Spence et al., "A Laser-Locked Cavity Ring-Down Spectrometer Employing an Analog Detection Scheme," Review of Scientific Instruments, vol. 71, No. 2, pp. 347-353, Feb. 2000.

Sze, "Physics of Semiconductor Devices." pp. 763-765, John Wiley & Sons, N.Y., 1982.

Tayebati et al., "Microelectromechanical Tunable Filter with Stable Half Symmetric Cavity," Electronics Letters, IEE Stevanage, GB, vol. 34, No. 20, pp. 1967-1968, Oct. 1998.

Tayebati et. al., "Widely Tunable Fabry-Perot Filters Using High Index-Contrast DBRs," Design and Manufacturing of WDM Devices, Dallas, Texas, Nov. 4-5, 1997, SPIE vol., 3234, pp. 206-218, 1998.

Yang et al., "Back-Illuminated GAN/AIGAN Heterojuction Photodiodes With High Quantum Efficiency and Low Noise," Applied Physics Letters, vol. 73, No. 8, pp. 1086-1088, XP000777678, Aug. 24, 1998.

Gillis et al., "Photoacoustic Spectroscopy for Quantitation of Trace Gases in Air," Chemical Science and Technology Laboratory National Institute of Standards and Technology, Industrial and Analytical Instruments and Services Forensics and Homeland Security, 2 pages, prior to Jul. 21, 2008.

Siegman, "Lasers, Chapter 11: Laser Mirrors and Regenerative Feedback," 5 pages, 1986.

\* cited by examiner

CRDS MIRROR FOR NORMAL INCIDENCE FIBER OPTIC COUPLING

This application is a continuation-in-part of U.S. patent application Ser. No. 11/770,648, filed Jun. 28, 2007, which is a continuation-in-part of U.S. patent application Ser. No. 11/633,872, filed Dec. 4, 2006.

U.S. patent application Ser. No. 11/770,648, filed Jun. 28, 2007; U.S. patent application Ser. No. 11/633,872, filed Dec. 4, 2006; and patent application Ser. No. 10/953,174, filed Sep. 28, 2004, now U.S. Pat. No. 7,145,165, are hereby incorporated by reference.

BACKGROUND

The present invention pertains to sensors and particularly to cavity ring down sensors. More particularly, the invention pertains to the structure of the sensors.

SUMMARY

The invention is a cavity ring down sensor having a fiber optic element coupled at a normal to a surface of the input mirror of the cavity of the sensor.

DESCRIPTION

The present invention may permit a fiber optic element to be easily mounted to a mirror so that light can be injected into the CRDS cavity from an external laser. This appears particularly important for the case of a CRDS system mounted in, for instance, a two inch well head with little room for the fiber to bend. Also the invention may provide an ability to fine tune the system so that the light from the fiber can be optimized in the cavity.

Two substrates of different materials may be mounted against each other with their common face at an angle relative to the normal to the mounting axis. The angle between the two substrates may be defined by the indices of the materials and be chosen so that light normal to the mounting axis and delivered along this axis by the fiber element is refracted into the cavity at an angle that is one of the beam leg directions. This approach may couple the light into the cavity efficiently.

The inner element (for instance, having $SiO_2$) may be optically sealed to the block. The second element (for instance, having Si) may be allowed to translate across the surface of the $SiO_2$ substrate thus providing fine tuning for the position of the fiber which is mounted to the backside of the Si substrate. For optimal performance, the external surfaces should be coated with an antireflection coating.

The mirror may be attached to the CRDS cavity so that light is made to enter the cavity. The position of the wedge to which the fiber is attached may be fine tuned for a maximum fluence into the CRDS cavity. Once achieved, the whole device can be potted to lock in the fine tuned position if desired.

For ground water measurements, the block may be lowered into a well, the block being in a liquid water tight chamber. Vapors from the water may be transmitted through a membrane into the cavity where they are absorbed if the proper wavelength is put into the cavity. The use of this wedge mirror assembly may permit the fiber input to be normal to the CRDS cavity. This mirror should be transmissive and so the inner element made of $SiO_2$ may be either a curve or a flat as opposed to one with a transducer mounted on it for tunability. This system may work for wavelengths where both Si and $SiO_2$ transmit the input radiation. An SWIR band between 1.5 and 2.0 microns may be one of the wavelength ranges of input radiation where the gases have significant absorption.

Figure 1:
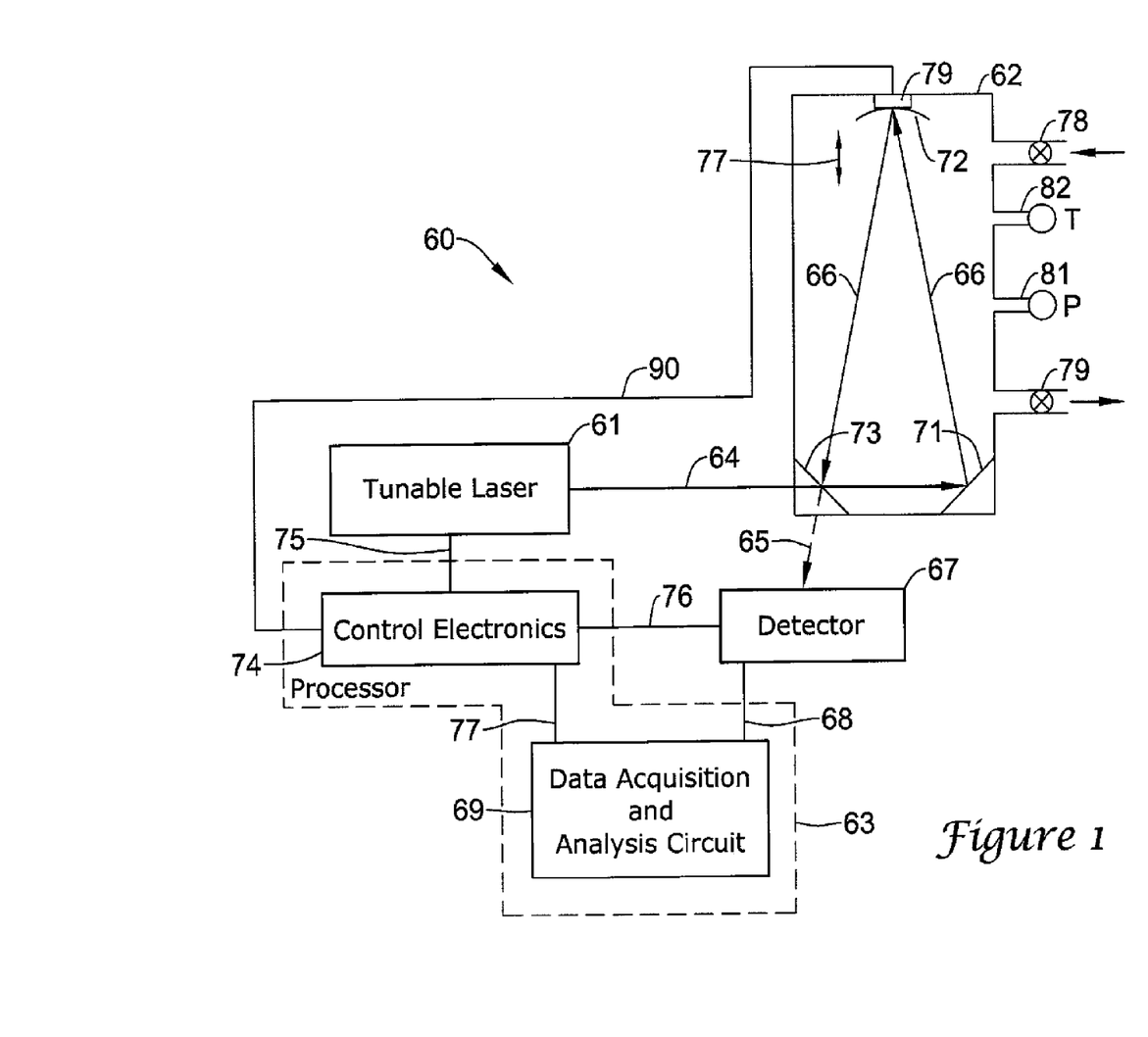
FIG. 1 is a diagram of a ring-down cavity.

As shown in FIG. 1, a tunable laser 61 may be coupled to a three mirror optical ring-down cavity 62. One of the mirrors, e.g., mirror 72, may have a slight and high radius curvature to improve stability so that a light beam 66 does not walk off the cavity. Cavity 62 may be a block ring cavity or, alternatively, a ring cavity akin to a cavity of laser system though not necessarily having two lasers going through it. Cavity 62 may have two, three, four mirrors, or any other number of mirrors providing a light path selected from various possible routes for light in the cavity. There may be an analog detection circuit 63 to extract the ring-down rate from an exponentially decaying ring-down waveform. A technique may be used to measure trace concentrations of gases in the near infrared region using a continuous wave excitation 64 of a cavity-ring down spectroscopy cell or cavity 62 (CW-CRDS). Cavity ring-down spectroscopy may be an absorption technique in which light 64 is coupled into a high finesse optical resonator 62. The cavity 62 may be tuned to the absorption line of the gas in the cavity being sensed and quantitatively measured. Cavity 62 may be tuned such that light 66 is in phase with the incoming light 64. This tuning, such as adjusting the path length of light 66, may be applicable to other kinds of cavities, such as those with two mirrors, four mirrors, and the like. Tuning the cavity with mirror 72 adjustment 77 with an actuator 79 may be one way of adjustment. Similarly, a light source 61 may have an output wavelength tuned to the absorption line of the gas in the cavity. By monitoring the decay rate of the light 66 inside the cavity with detection circuit 63 which includes a detector 67, one may determine a concentration of a particular gas in the cavity 62. The near infrared light 65 detected may contain vibrational overtone transitions and forbidden electronic transitions of various atmospheric species of gas. System 60 may obey Beer's law and provide a highly accurate concentration determination. The effective path length of the light 66 in the cavity may be about a hundred times larger than the physical size of the cell 62 due to highly reflective dielectric mirrors 71, 72 and 73. Mirror 72 may have an adjustment 77 for tuning the path length of cell 62 for light 66.

There may be fast trace gas impurity measurements of critical molecules such as trichloroethylene (TCE), dichloroethylene (DCE), $H_2O$, CO, $NH_3$, HF, HCl, $CH_4$ and $C_2H_2$. Such measurements may be made in seconds. Trace moisture concentration may be measured at levels from parts per billion (ppb) to parts per trillion (ppt).

Tunnel laser 61 may send a continuous wave (or possibly pulsed) light signal to cell 62. Signal 64 may be regarded as a signal 66 that is reflected around in cell 62 from mirror 71, to mirror 72, to mirror 73, to mirror 71 and so on until the signal 66 diminishes. Some light 65 may leave cell 62 and impinge detector 67. Detector 67 may convert light signal 65 to an electrical signal 68 that goes to a data acquisition and analysis unit 69. Control electronics 74 may send control signals 75, 76 and 77 to tunable laser 61, detector 65 and data acquisition and analysis unit 69, respectively. Also, a control signal 90 may be sent to a moveable support 79 of mirror 72 to provide tenability of the path for light 66. Support 79 may be a piezoelectric transducer to allow tuning and modulation of the path length of cell 62.

One may detect a certain fluid using a laser tuned on a transition band, near a particular frequency. A fluid may be a gas or liquid. Using system 62, one may be able to measure the concentration of the fluid in some medium. The certain fluid and associated medium may enter a port 78 and exit a port 79. Port 81 may be for a connection to a pump. Port 82 may be used for a gauge. One or more hollow optical fibers to and from the ring cavity may be used provide gas to take gas from the ring cavity. The gas may be compartmentalized in the cavity with Brewster windows.

The system 60 may provide for an intrinsic measure of absorption. The CRDS sensitivity may equal $$(\Delta t/t)(L_{opt}/L_{cav})(1/F_{acq})^{1/2}$$

Another relationship may be:

$$L_{opt} \sim L_{cav}\sqrt{[n_{mirror}(1-R)]} \sim 10^4 L_{cav}$$

Typical sensitivity may be at about $10^{-6}$ to $10^{-10}$ cm$^{-1}$ for multimode light and about $10^{-9}$ to $10^{-12}$ cm$^{-1}$ for single mode light.

The system 62 may be built on the strengths of a MEMS etalon, various laser system technologies and VCSELs. A laser gyroscope cavity may be used as a ring-down cavity.

Figure 2:
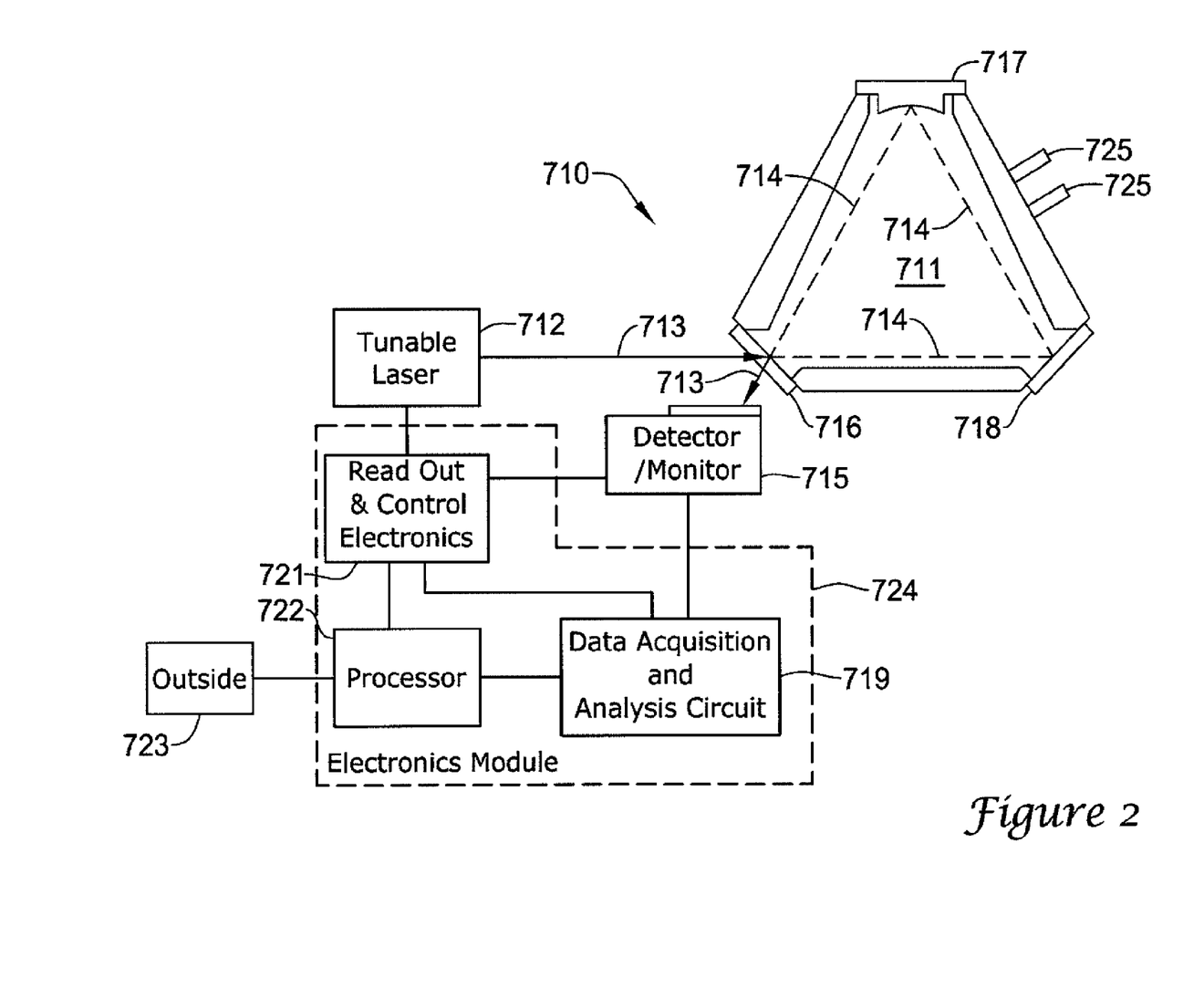
FIG. 2 is a diagram of a sensor system having a ring cavity which may be fabricated, formed, machined, or the like from one or several pieces of solid material.

FIG. 2 shows a sensor system 710 having a ring cavity 711. The cavity may be fabricated, formed or machined, or the like from one or several pieces of solid material. A light source 712 may emit a beam of light 713 into cavity 711. The beam of light may follow a path 714 of the cavity 711. Here, the light may propagate in a counterclockwise direction from the perspective of looking into the plane of the sheet of the Figure. A detector 715 may be proximate to where light 713 entered the cavity 711 from source 712. Source 712 may, for example, be a tunable laser.

At the corners of cavity 711, there may be mirrors 716, 717 and 718. Mirror 716 may partially reflect light 713 in the cavity so that detector 715 may detect some light in the cavity for analysis purposes. On mirror 716 may have a small hole for input and output for light 713. In this case, the mirror 716 may be fully reflective. Detection of light 713 may note intensity versus time, frequency, and other parameters as desired. The output of the detector or monitor 715 may go to a data acquisition and analysis circuit 719 for such things as acquisition, analysis and other purposes for obtaining information about a sample fluid in the cavity 711. One purpose may be for tuning the laser 712 to an adsorption line of the sample. The detector output to the readout and control electronics 721 may be improved with a dual JFET amplifier. Other circuits may be utilized for detector output processing. Readout and control electronics 721 may provide an excitation and control for light source 712. Inputs and outputs may be provided to and from a processor 722 relative to connections between the processor 722 and readout and control electronics 721 and data acquisition and analysis circuit 719. Processor 722 may also be connected to the outside 723 signals going in and out of system 710. A user interface may be effected with the readout and control electronics 721 and/or the outside 723. Readout and control electronics 721, data acquisition and analysis circuit 719, and processor 722 may constitute an electronics module 724. Electronics module 724 may have other components. Ports 725 may provide for input and output of a sample fluid to and from the cavity 711.

Figure 3:
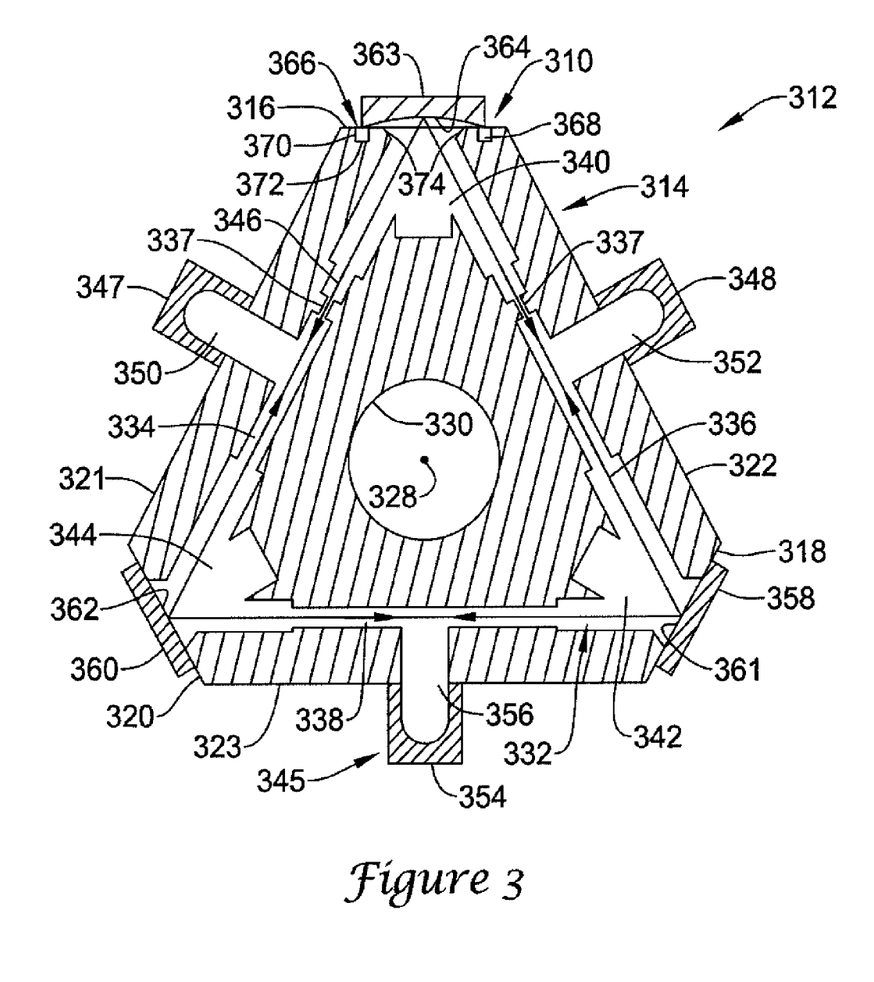
FIG. 3 is a diagram of the sensor system incorporating a machined-like block for the ring cavity.

A mirror mounting device 310 and approach for beam path alignment of a system 312 are illustrated generally in FIG. 3. The system 312 includes a system frame or block 314. The block 314 is generally triangular shaped with a hexagonal outer periphery. The shapes could be square, pentagon-like or other, along with various shapes for the periphery. The hexagonal outer periphery includes three planar non adjacent sides that form first, second and third mirror mounting surfaces 316, 318 and 320, respectively, and three further planar non adjacent sides 321, 322 and 323, respectively. The mounting surfaces 316, 318 and 320 and sides 321, 322 and 323 form a border for planar top and bottom surfaces 324 and 326, respectively, of the block 314. The block 314 is centered about an input axis 328 (which is perpendicular to top and bottom surfaces 324 and 326) within a circular inner boundary 330 of the block 314. The block 314 is formed of a glass ceramic or like material. Suitable block materials include the glass ceramic material marketed under the trademarks "Cervit" and "Zerodur". A suitable glass material is marketed under the trademark "BK-7".

As seen in FIG. 3, an internal optical cavity 332 of the block 314 comprises three substantially straight bores 334, 336 and 338, respectively, that are interconnected at the mounting surfaces 316, 318 and 320 by three cylindrical shaped wells 340, 342 and 344, respectively. The block 314 may be solid and then machined to accommodate various shapes, channels, holes, bores, and spaces for operational aspects or for placement of components. The bores 334 and 336 include apertures 335 and 337, respectively, that define a desired closed loop optical path. The bores 334, 336 and 338 and the wells 340, 342 and 344 are bored within the block 314 to form the triangular shaped closed loop optical path, with the mounting surfaces 316, 318 and 320 located at corners of the optical path.

As seen in FIG. 3, two planar mirrors 358 and 360, respectively, having flat reflective surfaces 361 and 362, respectively, are secured (for example, via optical contact, epoxy bonding or fritting) to the second and third mirror mounting surfaces 318 and 320, respectively. A curved mirror 363, having a concave reflective surface 364 is secured (via epoxy bonding or fritting) to the mirror mounting device 310 associated with the first mirror mounting surface 316. The reflective surface, 361, 362 and 364, of each of the mirrors 358, 360 and 363, reflects the light beam(s) 346 at its respective corner of the closed loop optical path defined by the optical cavity 332. Mirror 358 and/or mirror 360 may have a partially reflective surface so that its respective port may be used as an input and/or an output for such applications as a cavity ring-down sensor as an illustrative example.

Trace gas detection and identification with very high sensitivity may be achieved using cavity-ring-down technique implemented with ring-laser gyro fabrication and alignment technology in order to achieve cost-effective producibility.

The advantages of adapting ring laser gyro fabrication methods (laser block, mirror fab, attachment, and alignment, and so forth) may achieve a cost-effective system for cavity-ring-down gas detection. The present system has an approach for coupling light into and out of the ring cavity. In particular, the approach provides for directing light incident from the source normally onto the optical input port of the ring cavity in order to facilitate alignment of the source to cavity, and then interposing a prism coupling module to direct the light into the ring cavity. A variation of this approach includes a modification of the coupling prism introduced before the optical input port so as to also couple light in the cavity to an external detector, thus allowing the same cavity port to be both an input and output port without return light being fed back into the source.

Figure 4:
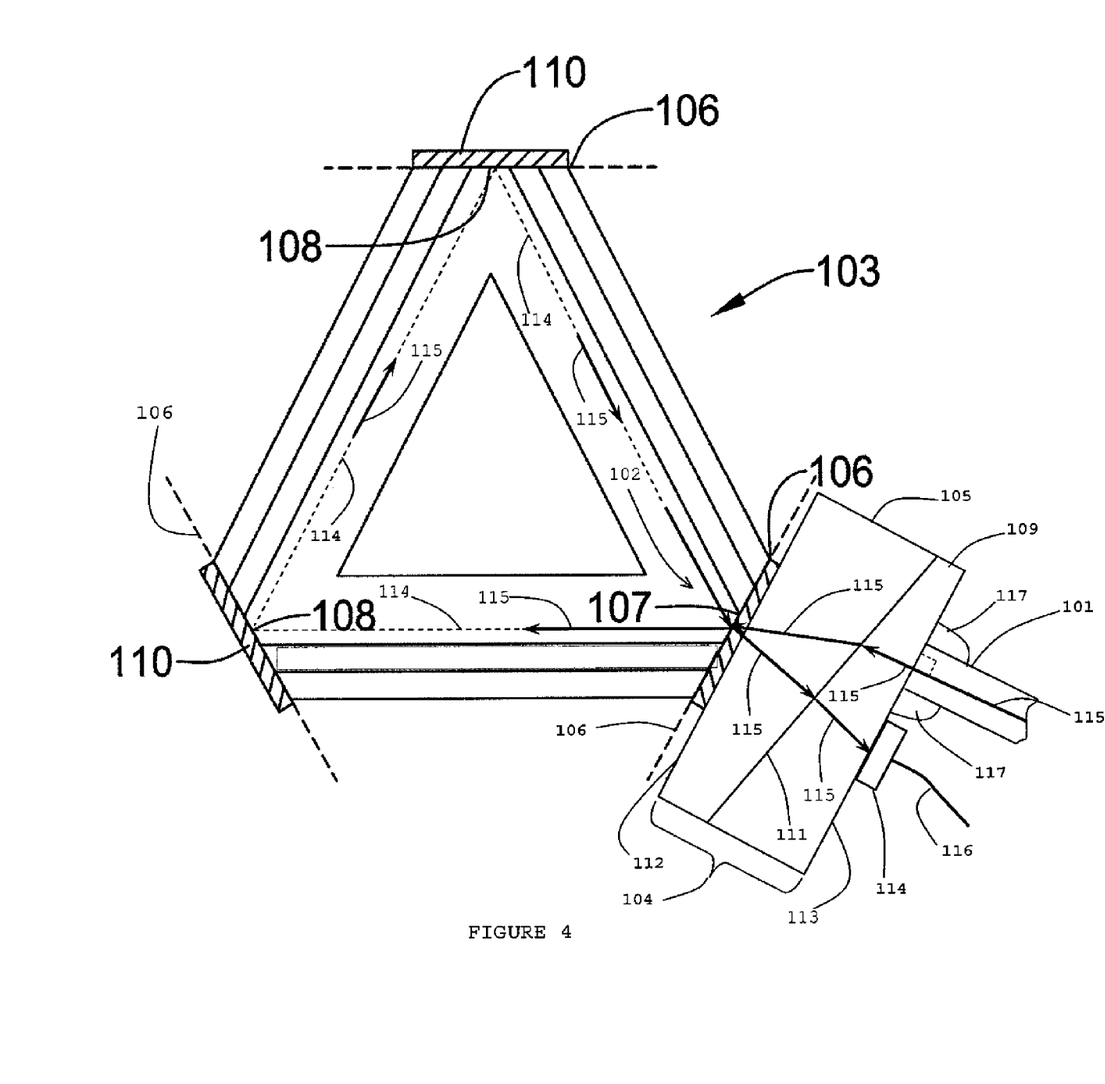
FIG. 4 is a diagram of a basic layout of a sensor with an illustrative example of the invention.

FIG. 4 shows a basic layout of a ring cavity 103 with three corners 102 and 108 for reflecting light around in the cavity along a path 114. Each of these corners may have external optically finished (polished) planar surfaces 106 as indicated by dashed lines. The inner face of a coupler or interface 104 may have a high reflectance optical coating 107, which may be regarded as a mirror 107, which is next to and parallel with the surface 106. High reflectance mirrors 110 may be attached to the other cavity ports or corners. One or more of the mirrors 110 may have a slight radius of curvature to facilitate optical stability of the cavity 103. One or more of the mirrors 110 may be integrated with a transducer (piezo-driven or otherwise) to move and tune the cavity into optical resonance.

FIG. 4 also shows an optical fiber-to-mirror interface 104 which may appear as a block 104. Block or interface may have two portions 105 and 109 which are adjacent to each other at a common border or surfaces 111. Portions 105 and 109 may be in contact at their respective surfaces 111 and optically coupled to each other. Portion 105 may have a surface 112 opposite of surface 111 that is in contact with a surface of mirror 107 and is optically coupled to mirror 107. A surface 113 opposite of surface 111 of portion 109 may be used for optical coupling of light into and out of cavity 103 from outside of the cavity ring down apparatus.

A light conveyance mechanism or channel or an optical fiber 101 may convey light into cavity 103 via the interface 104 and mirror 107. If situated appropriately on surface 113, light conveyance mechanism 101 may convey light out of cavity 103 via mirror 107 and interface 104. Or light may exit the cavity to a light detector 114 with an electrical signal indicating a light signal on a conductor 116. For an illustrative example, optical fiber may be situated with an end optically in contact with portion 109 via surface 113. The core of the fiber 101 conveying the line may be parallel to a normal of surface 113 or perpendicular to surface 113. Also, a light beam 115 may be perpendicular to surface 113 as it enters portion 109 and go straight to portion interface 111. At interface 111, light beam 115 may deviate from the straight path and head in another direction due to a different index of refraction of portion 105 relative to the index of portion 109. The path of light 115 may be calculated with Snell's law, $n_1 \sin \theta_1 = n_2 \sin \theta_2$. Light 115 may again be refracted as it enters cavity 103. The index of refraction may be regarded as the same as air. The path of light 115 may be determined with certain dimensions of portions 105 and 109, among other parameters and factors, including the indices of refraction of the materials traversed by light 115. The surfaces 113 and 112 and mirror 107 may be designed to be parallel; however, other approaches may be implemented.

Examples of materials for portions 105 and 109 may include fused silica and silicon, respectively. The silica may have an index n of about 1.46. Silicon may have an index n of about 3.6.

Light 115 may go in a clockwise direction along the optical path 114 which makes direction changes at two corners 108 due to mirrors 110, respectively, and corner 102 due to mirror 107. Since mirror 107 may be semitransparent, some light 115 may go through mirror 107, portion 105, interface 111 and portion 109 to detector 114 for amplitude measurement. The amount of amplitude of the returning light 115 at detector 114 may be indicative of a certain gas in the cavity, particularly such as after the light entering cavity from conveyance or fiber 101 ceases. A decrease of the amplitude of light 115 may be regarded as a ring-down or decay of the light 115 in the ring-like path 114 of cavity 103. Conveyance mechanism or fiber 101 may be attached to and/or secured into its perpendicular position relative to surface 113 with a fastener, epoxy 117, or the like.

Figure 5:
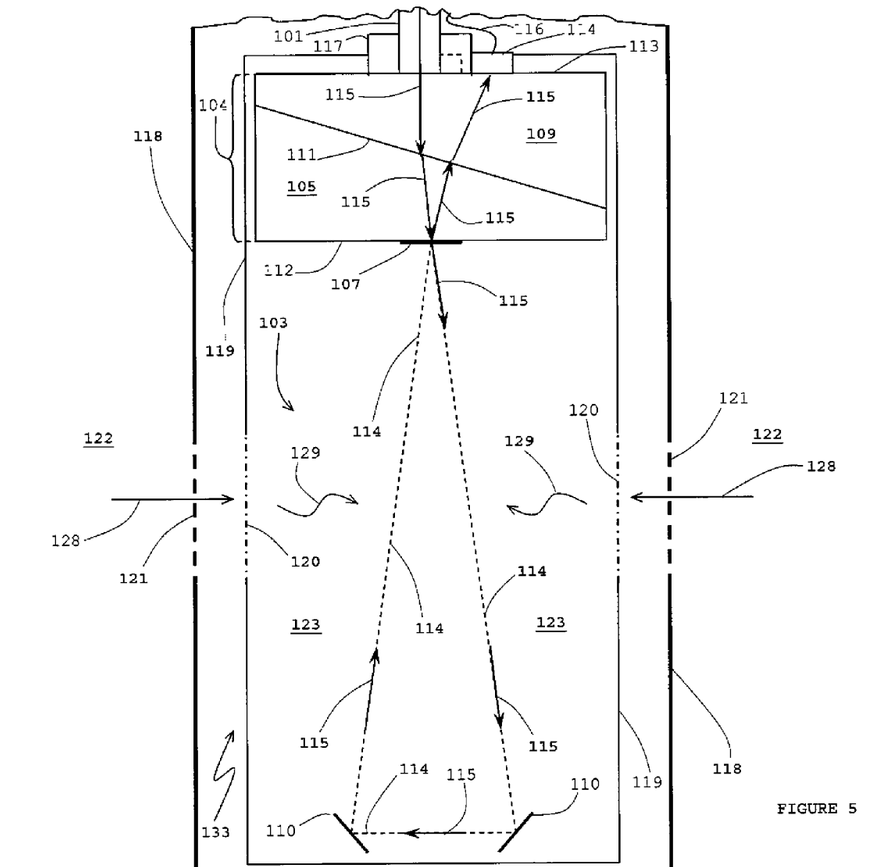
FIG. 5 is a diagram of a ring cavity sensor with an optical fiber to ring cavity interface.

FIG. 5 is a diagram of sensor cavity 103, situated, as an illustrative example, in a well casing 118 of a water well. Cavity 103 may be enclosed by a housing 119. There may be a portion or window of a screen 121 in the casing 118 at a certain depth of the well where water testing may be desired. Water 128 may seep through screen 121 from ground water area 122 into an area 123 within the casing proximate to housing 119 of cavity 103. Vapor or gas 129, if any, from the water may seep inside of the housing 119 of the cavity 103 through a membrane 120 at a portion or window of the housing 119. A pulse or duration light 115 at a certain amplitude may be introduced into the ring cavity 103 and the ring-down of the light may be measured via a detector 114. The characteristics of the decay may be measured for determining a presence of gas and a kind or identification of gas 129, if present in cavity 103.

Figure 6:
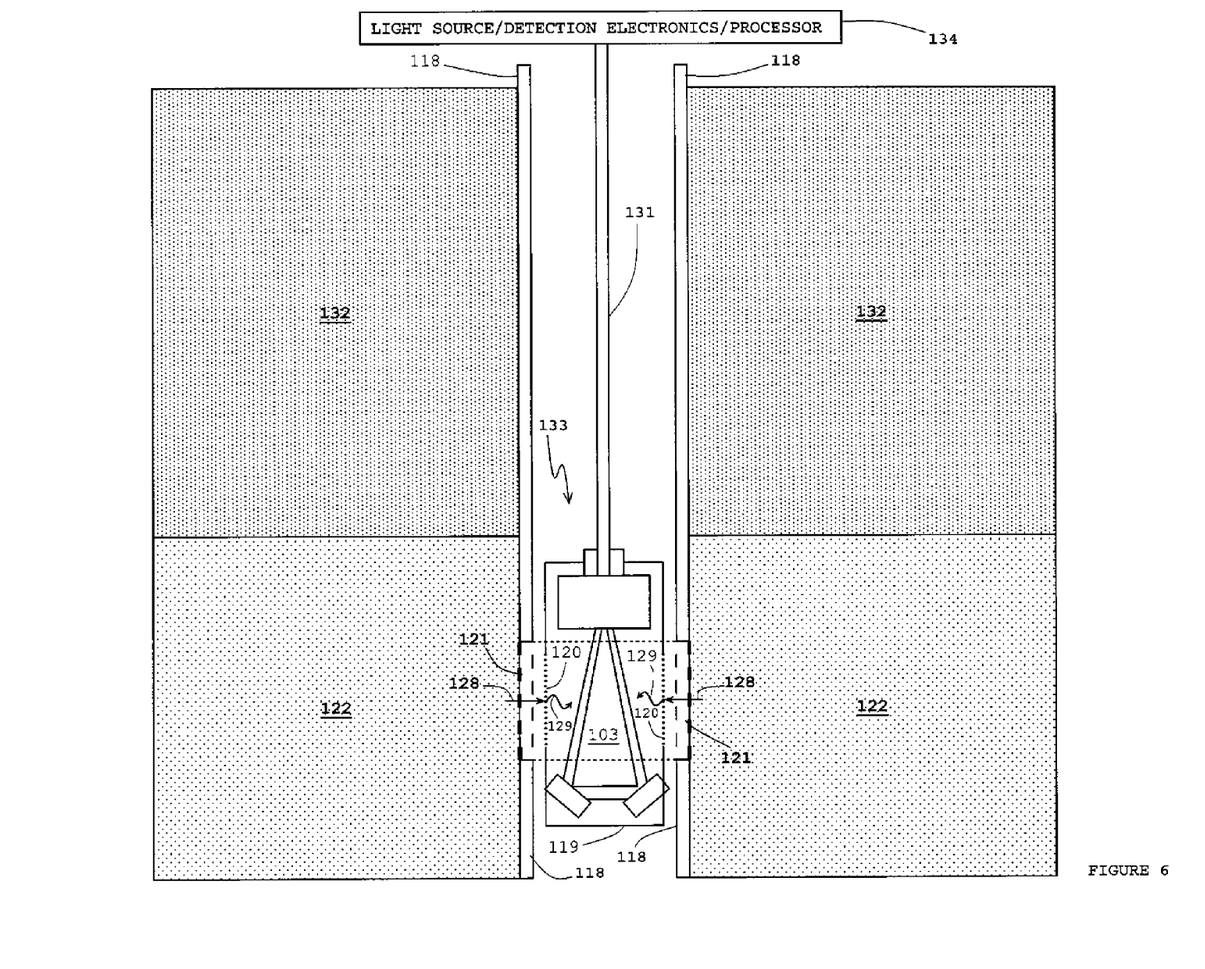
FIG. 6 is a diagram of the ring cavity sensor situated in a well casing.

FIG. 6 is a diagram of the sensor assembly 133 in a well casing 118 situated at a ground water 122 level. Above this level is a vadose zone 132 which relates to water that is located in the zone of aeration in the earth's crust above the ground water level. A cable 131 may hold sensor assembly 133 in suspension in the well casing 118 while testing for gases 129, if any, in the ground water 122 through the screen portion of the casing. Cable 131 may be connected to a module 134. Module 134 may have a light source, detection electronics and a processor. Other equipment may be incorporated in module 134 as needed for control of assembly 133, analysis for results, and so forth. Cable 131 may contain optical fiber 101 and connecting conductor 116 for detector 114. Fiber 101 may be connected to the light source in module 134. Detection electronics may receive and condition signals from the detector 114 via conductor 116. The processor may control the light source, process signals from the detection electronics and provide results of the sensing by the assembly 133. The source may provide light 115 through fiber 101 in cable 131 to sensor assembly 133 containing cavity 103.

Figure 7:
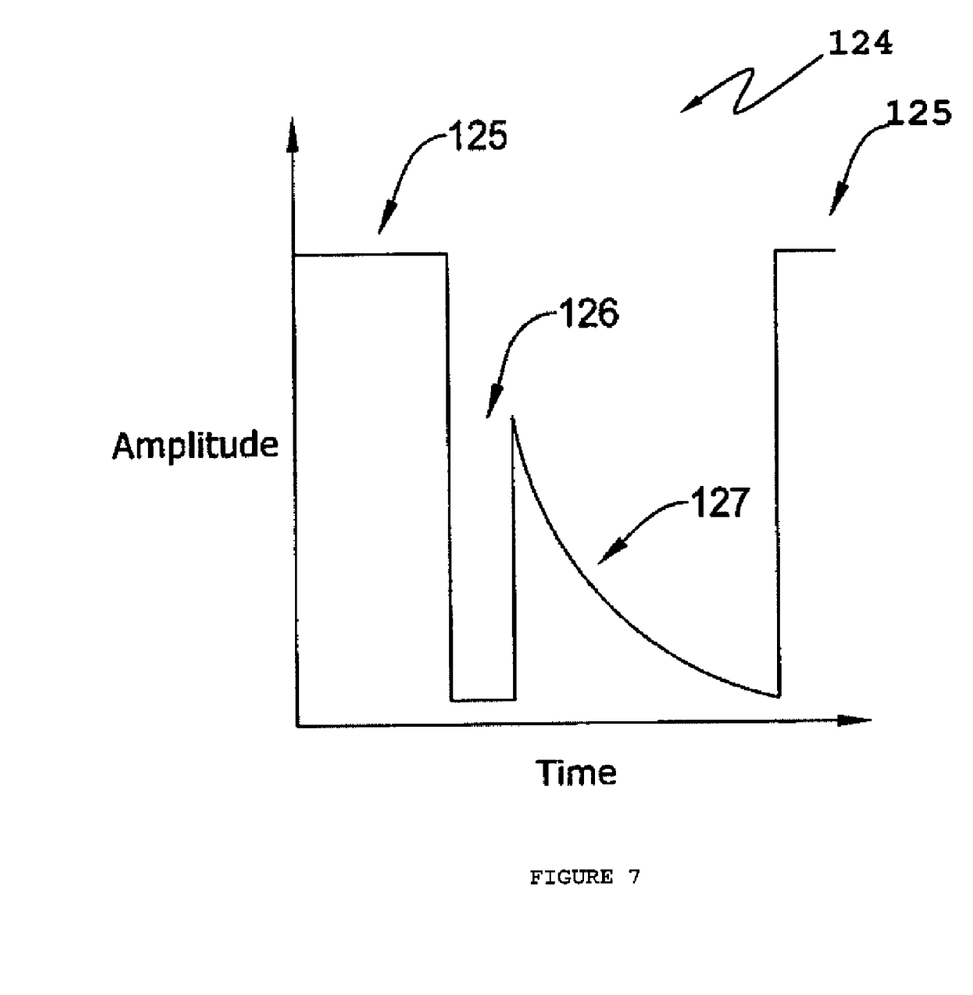
FIG. 7 is a graph showing intensity of light in the cavity ring down sensor during operation.

FIG. 7 is a graph 124 of an application of the cavity of the device shown in some of the Figures discussed herein being utilized as a cavity ring down sensor. The graph shows amplitude versus time. A detector 114 of the setup shown in FIGS. 4-5 may be a multi-function detector which senses intensity of light to the cavity 103 in one function, as shown by a portion 125 of graph 124. Another function of detector 114 may include a coupling to the cavity at portion 126 and measuring the light signal in the cavity at portion 127 after a supply of light to the cavity ceases at the coupling portion 126. Portion 127 shows a decay of the cavity light amplitude in the cavity ring-down device. The amplitude and the time of the ring down may provide information about a sample fluid (e.g., gas) which may in the cavity 103. Portions 125, 126 and 127 may be repeated. Also, wavelength of the light and absorption properties of the sample may affect the decay. A processor (e.g., processor 63, 722 or 134 of FIGS. 1, 2 and 6, respectively) along with other items such as tables and algorithms may aid in determining information about the sample.

Figure 8:
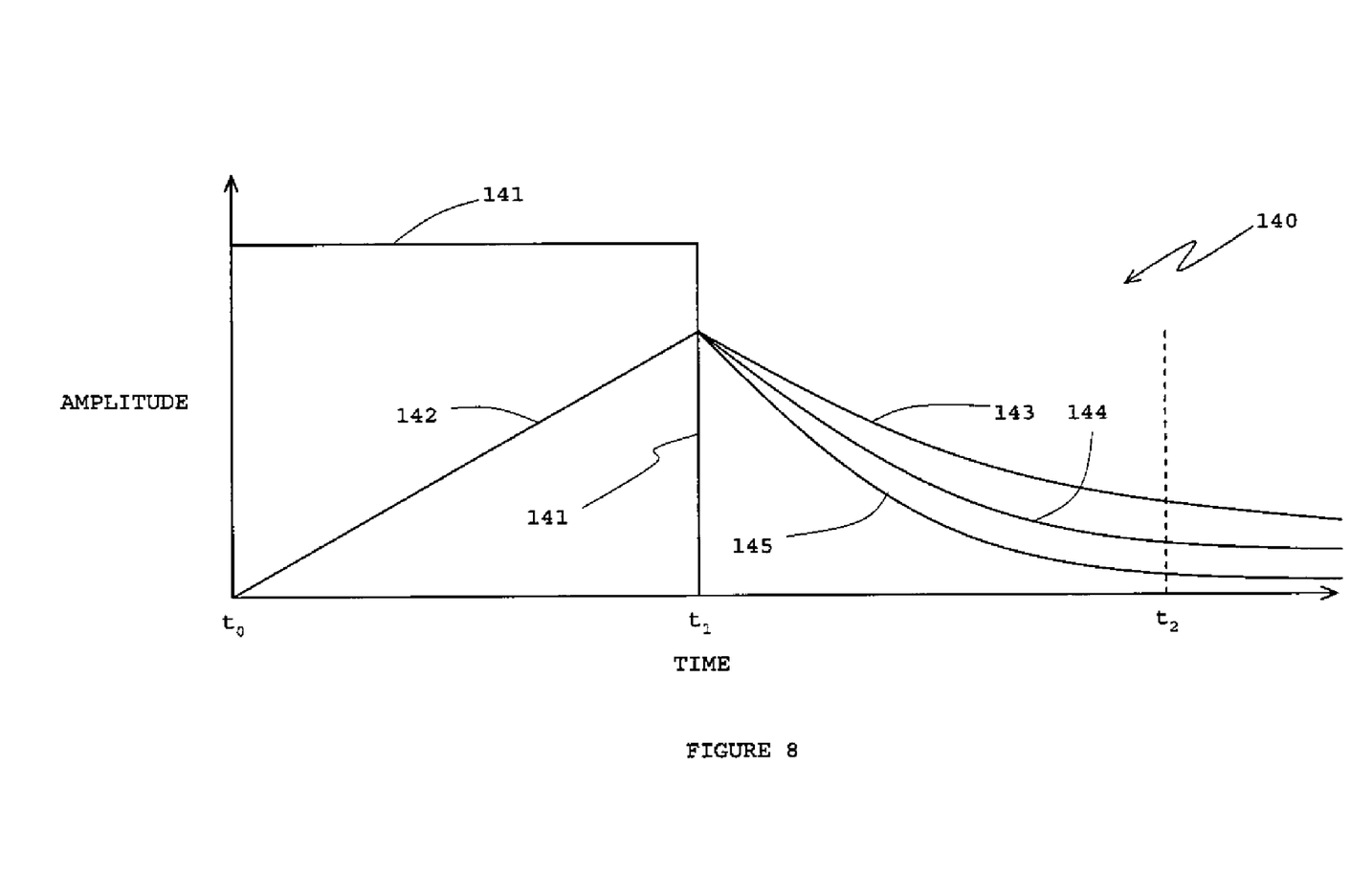
FIG. 8 is a graph of the decay intensities in the ring down cavity for various gases.

FIG. 8 is a graph 140 of amplitude versus time showing the light 115 behavior in cavity 103 on the present system. Signal 141 is an input of light 115 to cavity 103 via fiber 101, interface or block 104 and mirror 107, for a set period of time from $t_0$ to $t_1$. Curve 142 shows a build-up of light 115 amplitude along path 114 in cavity 103 while light 115 is incoming to cavity 103. At the time $t_1$ when the incoming of light 115 ceases, then the amplitude of light 115 along the ring-like path in cavity 103 begins to decrease (i.e., ring-down) as indicated by curves 143, 144 and 145. Curve 143 may illustrate an instance of light 115 signal ring-down when no gas other than air is present in cavity 103. Curve 144 may illustrate an instance of light 115 signal ring-down when a first gas is present in cavity 103 and curve 145 may illustrate an instance of light 115 signal ring-down when a second gas is present in the cavity. One may note that at $t_2$, the second gas reveals a greater decay than the first gas. Some causes may include different characteristics or properties, such as cross-section, concentration and/or absorption of the respective gases. This and other information may enable determining identification, amounts and other things of gases in the cavity. Processor 134 may provide such and other determinations about the gases along with the aid of other resources (e.g., internet, databases, and so forth) accessible by the processor.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A fluid sensor comprising:
   a plurality of mirrors forming a closed light path;
   a refraction block having a first surface proximate to the plurality of mirrors; and
   a light channel attached to a second surface of the refraction block at a normal of the second surface;
   wherein the light channel is associated with a structure sufficient for holding the refraction block and the plurality of mirrors in suspension within a sampling environment.

2. The sensor of claim 1, wherein the light channel extends approximately straight from the second surface of the refraction block when the refraction block and the plurality of mirrors are held in suspension.

3. The sensor of claim 2, wherein a light path proceeds through the light channel in a direction approximately perpendicular relative to the second surface of the refraction block, through the refraction block and in the closed light path.

4. The sensor of claim 3, wherein the light channel comprises an optical fiber.

5. The sensor of claim 3, wherein:
   the refraction block comprises:
   a first portion having a first index of refraction; and
   a second portion adhered to the first portion; and
   the second portion has a second index of refraction.

6. The sensor of claim 3, further comprising:
   a detector for detecting light of a ring-down from the closed light path; and
   wherein an amplitude and/or period of a ring-down in the closed light path is for providing information about a fluid in the closed light path.

7. The sensor of claim 6, wherein light for the closed light path is infrared.

8. The sensor of claim 3, further comprising:
   a enclosure for holding the plurality of mirrors and refraction block; and
   wherein:
   the enclosure has at least one opening;
   the at least one opening is covered with a membrane for permitting gas but not liquid to pass through to the plurality of mirrors;
   the enclosure is for placing the plurality of mirrors in a well casing; and
   the well casing has a screen at a certain level for permitting fluid to enter the well casing and be proximate to the membrane of the enclosure.

9. The sensor of claim 8, wherein the plurality of mirrors is situated in a ring laser gyroscope cavity.

10. A cavity ring-down system comprising:
    a cavity having a ring-like light path;
    a refractive interface optically coupled to the cavity;
    an optical fiber having a first end attached to the first surface of the interface; and
    wherein the refractive interface is for directing a light beam from approximately perpendicular to a first surface of the interface into the ring-like light path;
    the optical fiber is for providing the light beam to the first surface of the interface; and
    the optical fiber is associated with a structure for suspending the cavity and the refractive interface within a sample environment.

11. The system of claim 10, wherein the longitudinal dimension of the optical fiber is approximately perpendicular to the first surface of the interface.

12. The system of claim 10, wherein:
    the optical fiber is approximately straight between a point for holding the structure and the refractive interface and approximately perpendicular to the first surface of the interface, while the refraction block and the cavity are held in suspension.

13. The system of claim 12, wherein:
    the interface comprises:
    a first block having the first surface of the interface and having a second surface; and
    a second block having a first surface adjacent to the second surface of the first block and having a second surface adjacent to the cavity;
    the first block has a first index of refraction; and
    the second block has a second index of refraction.

14. The system of claim 13, wherein the ring-like light path comprises a plurality of mirrors.

15. A method for providing a cavity ring-down system comprising:
    providing a ring-down optical path formed by a plurality of mirrors;
    providing an interface having a first surface adjacent to the ring-down optical path and proximate to the plurality of mirrors;
    making the interface with two layers of material having different indices of refraction; and
    attaching a light channel to a second surface of the interface to provide a light beam into the interface at a direction perpendicular to the second surface of the interface and through the interface into the ring-down optical path
    wherein the two layers are mounted against each other with their common face at an angle relative to the direction perpendicular to the second surface.

16. The method of claim 15, further comprising:
    designing the layers with dimensions so that the interface can guide an incoming light beam, perpendicular to the second surface of the interface, through the interface into the ring-down optical path.

17. The method of claim 16, wherein the light channel comprises an optical fiber.

18. The method of claim 17, further comprising:
    providing an enclosure for the ring-down optical path; and
    connecting a supporting line to hold the enclosure and interface; and
    wherein the optical fiber is approximately straight from the interface; and
    the enclosure comprises a portion having an opening covered with a membrane which permits entry of a gas and prevents entry of a liquid into the enclosures.

* * * * *